(12) United States Patent
Rabin et al.

(10) Patent No.: US 7,920,777 B2
(45) Date of Patent: Apr. 5, 2011

(54) CAPILLARY FORCE VAPORIZERS

(75) Inventors: Barry Hal Rabin, Idaho Falls, ID (US);
Charles Howard Sellers, Pleasanton, CA (US); Warren Saul Breslau, Berkeley, CA (US); Erick Matthew Davidson, El Cerrito, CA (US)

(73) Assignee: Vapore, Inc., Alameda, CA (US)

( * ) Notice: Subject to any disclaimer, the term of this patent is extended or adjusted under 35 U.S.C. 154(b) by 663 days.

(21) Appl. No.: 11/920,320

(22) PCT Filed: May 15, 2006

(86) PCT No.: PCT/US2006/018696
§ 371 (c)(1),
(2), (4) Date: Nov. 13, 2007

(87) PCT Pub. No.: WO2006/124757
PCT Pub. Date: Nov. 23, 2006

(65) Prior Publication Data
US 2009/0220222 A1    Sep. 3, 2009

Related U.S. Application Data

(63) Continuation-in-part of application No. 10/691,067, filed on May 16, 2005.

(60) Provisional application No. 60/681,825, filed on May 15, 2006.

(51) Int. Cl.
*F22B 29/06* (2006.01)
*F22B 37/18* (2006.01)

(52) U.S. Cl. ..................................... 392/396; 122/366

(58) Field of Classification Search .................. 392/396, 392/385–406; 122/366, 306–406.4
See application file for complete search history.

*Primary Examiner* — Daniel Robinson
(74) *Attorney, Agent, or Firm* — The Firenza Group Ltd.; Sharon R. Kantor (57) ABSTRACT

The present invention concerns capillary force vaporizers for use in vaporizing liquids and emitting pressurized vapors. In one embodiment, the inventive capillary force vaporizer includes a porous member, a heater component to convey heat to the porous member, and a vapor containment region. The porous member further includes a capillary network, a surface for receiving liquid and a vaporization area in which vapor is produced from the liquid. The vapor is collected and pressurized within the vapor containment region, which includes one or more openings for the release of vapor at a velocity greater than zero. Several different embodiments for capillary force vaporizers and systems comprising capillary force vaporizers are disclosed along with methods for their use.

15 Claims, 6 Drawing Sheets

CAPILLARY FORCE VAPORIZERS

The present invention is a continuation-in-part of commonly-assigned and co-pending application for U.S. patent Ser. No. 10/691,067 filed 21 Oct. 2003.

BACKGROUND OF THE INVENTION

1. Field of the Invention

The present invention relates to the vaporization of liquids and the pressurization of vapors in capillary force vaporizers. More particularly, the invention relates to improved capillary force vaporizers, as well as capillary force vaporizer modules and systems for producing vapor for a variety of applications.

2. Description of the Pertinent Art

Many applications utilize gases that have been generated from liquid sources. Vaporization devices have been designed to vaporize liquids and release the resulting vapor under pressure. In applications in which a pressurized vapor stream is desired, prior art devices generally require that liquid be supplied to the device under pressure, or that the vapor is otherwise pressurized by external means. For example, in pressurized boiler systems, liquids are generally required to be supplied under at least as much pressure as that of the produced vapor. Pressurized liquid sources are usually inconvenient to use, heavy to transport, potentially explosive, and prone to leakage. It is desirable, for many applications, to produce pressurized vapor streams directly from liquids that are either at or near atmospheric pressure. One class of devices that achieve this goal are known in the art as capillary pumps, capillary vaporization modules or capillary force vaporizers. These devices all generate pressurized vapor directly from unpressurized liquid by applying heat to cause liquid boiling within a capillary member, and by at least partially constraining the evolved vapor to allow pressure to increase, exiting the device through one or more orifices as a high velocity jet. Other features, which these devices have in common, are that they all are thermally powered, compact, and generally have no moving parts, thereby offering certain advantages over other techniques used for liquid vaporization and vapor pressurization. Capillary pumps, capillary vaporization modules, capillary force vaporizers and devices in which they may be found are variously described in U.S. Pat. Nos. 5,692,095; 5,870,525; 6,162,046; 6,347,936; 6,585,509 and 6,634,864.

While a number of the prior art devices mentioned above offer advantages over alternative liquid vaporization technologies, the devices were found to have certain limitations. First, some prior art capillary force vaporizers occasionally exhibited poor mechanical reliability. The devices relied upon a typically thin and brittle coating material for an impermeable peripheral sealing member. The sealing member, in association with the liquid filled porous member in which vaporization takes place, allows pressure to increase within the device and also provides structural integrity to hold the various components together in intimate contact. Under thermal gradients, internal pressure and temperature cycling experienced during certain device operation, the peripheral seal component is prone to cracking, occasionally resulting in reduced performance or premature device failure. As thermal stresses tend to increase with size, cracking was more common in larger devices. Attempts to generate larger capillary force vaporizers to meet higher output flow rate requirements needed for some applications therefore met with limited success.

Other disadvantages of certain prior art capillary force vaporizers were the relatively slow response time experienced in responding to changes in input heat or power, and limited energy efficiency. The slow response time and limited energy efficiency are thought to be a consequence of having to conduct heat from a heat source external to the device and far from the vaporization zone. This results in having an excess mass in contact with the vaporization member that must be heated or cooled before a change in the vaporization rate can take place, thus causing undesirable energy loss to the surrounding environment. Excess heater temperatures and resulting shorter lifetimes; fabrication issues in that additional surfaces are required to be smooth; and the extra complexity of requiring additional parts are other disadvantages associated with prior art capillary force vaporizers.

SUMMARY OF THE INVENTION

The present invention seeks to overcome certain limitations of, and make improvements to, the prior art by providing improved capillary force vaporizers for the vaporization of liquids and the pressurization of vapor. The capillary force vaporizers of the present invention feature novel configurations that provide better mechanical reliability and improved response times to changes in input heat and power, in addition to offering other advantages over prior art devices as will be discussed in greater detail below.

DETAILED DESCRIPTION OF THE INVENTION

Capillary force vaporizers of the present invention feature certain improvements over devices such as capillary pumps, capillary vaporization modules and like devices of the prior art. Somewhat surprisingly, it has been found that under certain circumstances, it is possible to eliminate the need for an insulation component as well as obviate the need for a seal around the periphery of such prior art devices.

Insulation layers or insulator components featured in prior art capillary pumps were employed in order to shield heat from reaching the liquid feed to the device, which was typically contained in some form of liquid reservoir. Such prior art capillary pumps required external heaters or some method of delivering heat to an exterior surface of the device, therefore the source of heat was not physically integrated into the vapor-generating portion of the device. A number of uses for these prior art devices included situations in which both high flow rate was required and the generated vapor needed to overcome some external system pressure. This combination required the devices to employ a thin, small pore size vaporizer component in combination with a thicker, larger pore size insulator component. In instances where the external back pressure anticipated or experienced on the vapor generated by a capillary force vaporizer is low, for example less than about 3 lbs/in$^2$ (0.21 kg/cm$^2$), which includes many important commercial uses, it has now unexpectedly been found that by careful selection and the proper combination of porous material properties and dimensions, a high flow rate device can successfully function using a unitary porous member that serves to function both as a vaporizer component and an insulation layer, obviating the need for both a vaporizer component and a separate insulator component.

In the instant invention, the unitary component that provides this dual vaporization and insulation functionality is simply referred to herein as the porous member. Suitable materials for the porous member have a mean pore size preferably between 0.5 μm and 100 μm, more preferably between 1 μm and 50 μm, and most preferably between 2 μm and 30 μm. Porosity of the porous member is preferably between 25% and 95%, more preferably between 30% and 90% and most preferably between 35% and 85%. In one embodiment of the present invention, the porosity of the porous member is about 50%. The porous member is provided in any useful shape that allows liquid to enter on one surface and vapor to be generated and released from another surface, for example disks, plates or tubes have been used. The thickness of the porous member is carefully controlled to ensure adequate thermal insulation and liquid permeability are both achieved. For most uses, the thickness of the porous member is varied between 0.05 cm and 5 cm. The porous member is preferably low thermal conductivity ceramic made by any processes known in the art that are capable of generating this unique combination of pore size and total porosity. Examples are alumina or zirconia produced by partial sintering of powder compacts, vacuum forming of powder, fiber and binder mixtures, or by any fugitive pore forming processes used for generating foamed structures.

Further, it has also been found that under certain circumstances, it is possible to eliminate the need for having a peripheral seal that previously surrounded a capillary pump in order for proper functioning of the device. In prior art devices, peripheral seals or sealing members were required in order to at least partially enclose the region in which vapor was generated in the device. Having a seal surrounding the device at the periphery helped to prevent the leakage of liquid, vapor or the combination of liquid and vapor from the device, as well as helping to reduce the loss of pressure of the vapor as it left the device.

Sealing members that were employed with prior art devices provided at least partial, and more usually, substantial enclosure of the vaporization region. Techniques used for peripheral seals or sealing members in the prior art included materials that exhibited low thermal conductivity such as shrouds constructed from rigid materials such as stainless steel, titanium alloys, or the like; glass seals, sintered ceramic coatings; etc., as well as combinations of the foregoing. By contrast, in the instant invention, it has been surprisingly discovered that by exerting sufficient compressive force on an orifice component, ejection surface or other appropriate housing or containment region via mechanical means, it is possible to virtually prevent the loss of liquid or vapor from the periphery of the capillary force vaporizer. Thus, it is possible to eliminate a peripheral sealing means that partially or substantially encloses the vaporization region of a capillary force vaporizer.

Briefly, therefore, a capillary force vaporizer according to one embodiment of the present invention is a device or method for generating pressurized vapor from unpressurized liquid, comprising:
1. a porous member further comprising a capillary network, a surface for receiving liquid, and a vaporization area in which vapor is produced from the liquid;
2. a heater component to convey heat to the porous member; and
3. a vapor containment region for the collection and pressurization of vapor, having one or more openings to release vapor at a velocity greater than zero.

The vapor containment region of a capillary force vaporizer of the present invention is that volume in which vapor collects, vapor pressure increases and where pressurized vapor is released through one or more orifices. This volume can be formed to the interior of the walls of a housing component. Therefore, according to an alternate embodiment of the present invention, a capillary force vaporizer is a device or method for generating pressurized vapor from unpressurized liquid comprising:
1. a porous member further comprising a capillary network, a surface for receiving liquid, and a vaporization area in which vapor is produced from the liquid;
2. a heater component to convey heat to the porous member; and
3. a housing component comprising one or more orifices for the release of vapor, and further defining a volume in which the vapor is collected and pressurized.

In prior art devices, as stated above, capillary pumps often exhibited poor mechanical reliability due to their reliance upon a typically thin and brittle coating material for the peripheral sealing member. In the present invention, the need for peripheral sealing means has surprisingly been obviated through the use of compressive mechanical force. By using mechanical means to engage the various components of the capillary force vaporizers of the present invention, it has been possible to allow pressure to build within the device, prevent the loss of liquid or pressure at the periphery of the device, and improve the structural integrity and rate of failure of the devices.

One technique in which compressive mechanical force is applied to engage the components of the capillary force vaporizers of the present invention is to use a suitable type of mechanical force generator such as a clamp or spring. Consequently, one description of such a mechanical force generator would be that it generates mechanical force by deflection of an elastic member. Thus, a capillary force vaporizer may comprise a collection of one or more springs or clamps. There may be one or more such mechanical force generating components within the capillary force vaporizer. According to a preferred embodiment of the present invention, two mechanical force components in the form of springs are used at diametrically opposing sides of a capillary force vaporizer.

Without being bounded by theory, it is suspected that the reason mechanical force can successfully be used in capillary force vaporizers of the present invention, in lieu of the peripheral seals used with prior art devices, is that, by proper selection of material and geometry, clamp or spring components can be designed to exert sufficient mechanical force on an internal vapor containment component to, in effect, act to substantially exclude liquid and vapor from escaping from the interface between the porous member and the internal vapor containment component. Accordingly, numerous techniques that may be regarded as comprising the generation of compressive mechanical force are contemplated. In addition to actual mechanical springs and clamping devices, other mechanical force means as between the internal vapor containment component and the porous member or among other components of the capillary force vaporizers of the present invention are understood to include: friction fittings; snap closures; bayonet attachments; threaded screw closures; twist-lock closures; as well as the various types of spring systems known to those skilled in the art, including conical washers, wavy washers, bent leaf springs and coil springs; welding; chemical, physical or mechanical bonding; sintering; chemical reaction; as well as combinations of any of the foregoing. Note that regardless of the nature of the method used to generate mechanical force as contemplated in the present invention, an important distinction between the present invention and prior art devices is that prior art devices featured a sealing member, coating or shroud peripheral to the device components. By contrast, the mechanical force mechanism of the present invention contemplates the application of compressive force among or between the various components of the device as the sole means for preventing leakage and for purposes of increasing pressure.

Accordingly, in an alternate embodiment, a device for the vaporization of liquid and the pressurization of vapor of the present invention may be regarded as comprising:

1. a porous member, comprising a capillary network, a surface for receiving liquid, and a vaporization area in which vapor is produced from the liquid;
2. a heater component to convey heat to the porous member; and
3. a vapor containment component, comprising a vapor containment region for the collection and pressurization of the vapor, a mechanical force generator and at least one orifice for the release of the vapor.

Additional examples and alternate embodiments of the present invention will be further elucidated through discussion below and through reference to the accompanying Figures.

Figure 1:
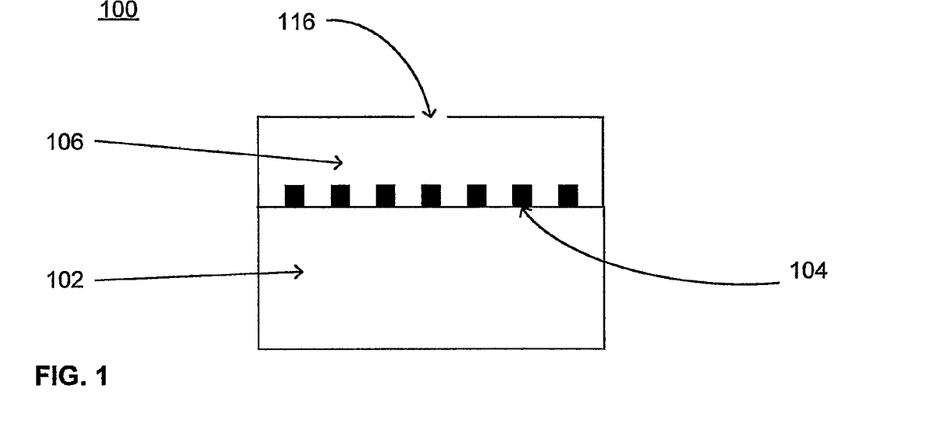
FIG. 1 is a schematic cross sectional view of a capillary force vaporizer in accordance with a first embodiment of the present invention.
Figure 2:
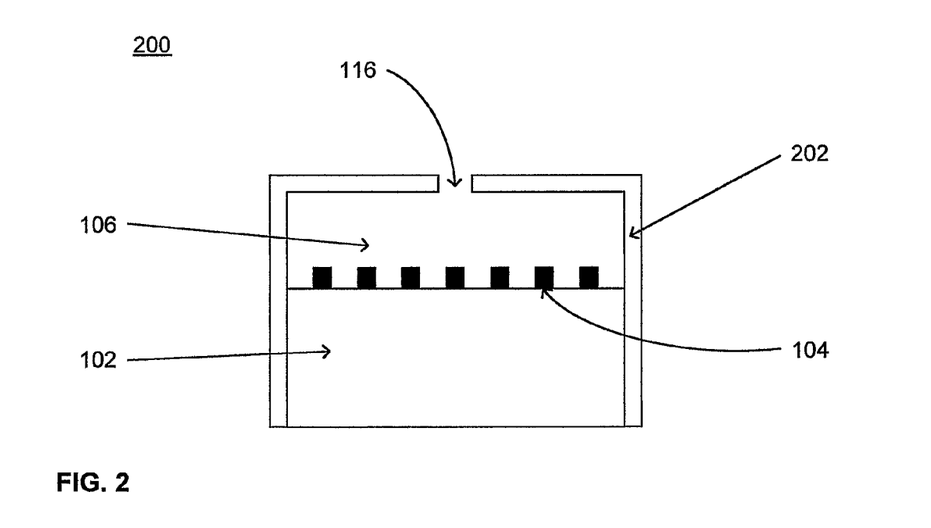
FIG. 2 is a schematic cross sectional view of a capillary force vaporizer in accordance with a second embodiment of the present invention.

FIG. 1 illustrates one embodiment of a capillary force vaporizer according to the present invention shown at 100. Thus, device 100 comprises porous member 102, heater component 104 and vapor containment region 106. An alternate embodiment of the present invention is shown in FIG. 2, which shows device 200 comprising porous member 102, heater component 104, and housing component 202. Housing component 202 further comprises one or more orifices 116 and also defines or, in other words, provides a bounded volume for the collection and pressurization of vapor at vapor containment region 106. Operation of capillary force vaporizers according to various embodiments of the present invention will now be discussed in greater detail with reference to the following Figures.

Figure 3:
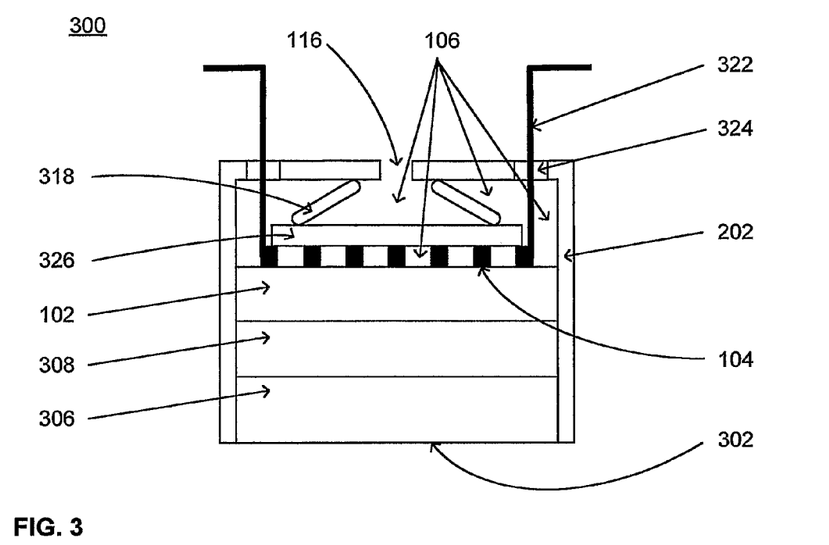
FIG. 3 is a schematic cross sectional view of a capillary force vaporizer in accordance with a third embodiment of the present invention.

During operation of capillary force vaporizer 300 of FIG. 3, liquid enters the device at liquid feed surface 302 and vapor is ejected from the device at one or more orifices 116. In the direction of flow of fluid, that is, liquid or vapor, device 300 comprises: optional liquid supply component 306, optional insulator component 308, porous member 102, heater component 104, optional support insulator 326, optional spring component 318, vapor containment region 106, housing component 202 and orifice component 116. Optional liquid supply component 306 and optional thermal insulation component 308 are porous material components that are optionally shown included in this embodiment and they are removed in instances where the unitary porous member alone is sufficient to achieve the desired device performance characteristics, as described previously. Optional liquid supply component 306 is used for example, when it is desirable to provide a separate element for interfacing with a liquid supply source, or when it is desirable to incorporate additional functionality into the device prior to vaporization, such as: liquid pretreatment, filtration and introduction of additional constituents, as well as combinations of the foregoing, as will be understood by those knowledgeable in the relevant art. Similarly, as discussed previously, optional thermal insulation component 308 is included when, due to certain combinations of high flow rate and output pressure requirements, as well as thermophysical characteristics of liquids or vapors, it is necessary to use a thinner, smaller pore size porous member for the vaporization component. Suitable materials for use with either optional liquid supply component 306 or optional thermal insulation component 308 are described in U.S. Pat. Nos. 6,634,864 and 6,585,509, and in patent application U.S. Ser. No. 10/691,067.

In FIG. 3, heat is provided to porous member 102 by heater component 104 disposed towards the interior of device 300 in direct heat-exchanging contact with porous member 102. Vaporization of liquid takes place within a region of porous member 102 at or near the interface of porous member 102 and heater 104. Generated vapor is contained within region 106. Compressive mechanical forces generated by friction between peripheral walls of housing component 202 and stacked components 102, optional 308 and optional 306 by optional spring component 318 effectively prevent leakage of vapor and liquid from inventive capillary force vaporizer 300, thereby allowing vapor pressure to increase at regions 106. Vapor is then released from orifice 116 with velocity greater than zero, where the actual velocity achieved depends on the rate of vaporization, the volume of region 106, and the shape and cross sectional area of one or more orifices 116.

According to a preferred embodiment of the invention, heater component 104 comprises an electric resistance heater. Optional spring component 318 and optional support insulator 326 may be used to ensure complete and intimate physical contact between heater 104 and porous member 102. Optional spring component 318 is but one example of a mechanical force generating component that may be used in accordance with the teaching of the present invention. A number of configurations that are acceptable for optional spring component 318 known to those skilled in the art are discussed above. The spring component preferably comprises a high stiffness material, that is, a material having a high elastic modulus, typically at least about $2 \times 10^9$ kg/m-sec$^2$ (approximately $2.9 \times 10^5$ lbs/in$^2$). Suitable materials for the spring component include, but are not necessarily limited to materials such as: steels and other metallic materials including titanium; alloys and aluminum; ceramics; plastics; as well as combinations of the foregoing.

Optional support insulator 326 is preferably comprised of a rigid, highly porous low thermal conductivity material. The thermal conductivity of the material is preferably less than about 50 W/m-° K and more preferably less than about 30 W/m-° K. The porosity is preferably greater than about 30 volume %, more preferably greater than about 40% and most preferably greater than about 50 volume %. Materials that are suitable for use for optional support insulator 326 include those such as partially sintered or rigid foam, ceramic or glass, that evenly distribute compressive forces generated by optional spring component 318 and prevent conduction of heat away from heater 104 and porous member 102, while not offering any substantial resistance to the egress of vapor from porous member 102 during operation. Examples of suitable materials for optional support insulator 326 include alumina and zirconia as well as combinations of the foregoing.

Electrical connections are provided to heater 104 by leads 322 that pass through housing component 202 via electrical feedthroughs 324 and that connect with heater 104. Electrical feedthroughs 324 can be formed by methods known to those skilled in the art, examples for which include: epoxy seals; glass seals; mechanical seals such as o-rings; as well as combinations of any of the foregoing. In cases where housing component 202 comprises an electrically insulating material, also referred to as a dielectric material, it is possible for leads 322 to make contact with housing component 202 without creating a short circuit. In such cases, electrical feedthroughs 324 may comprise a simple close tolerance hole in housing component 202. Where heater 104 is an electric resistance heater, it may be powered by connecting leads 322 to an external power supply (not shown) that may provide power characterized as either alternating current (AC) or direct current (DC)

Unlike prior art capillary pump devices, housing component 202 of device 300 no longer needs to act as a heat transfer component. In prior art devices, heat was conducted from outside the device via the device housing to the vaporizer component. By contrast. in the present invention, heater 104 is situated in heat-exchange contact with the vaporization member and does not make direct contact with housing 202. Therefore, fins or posts that served to conduct heat from a first or upper surface of prior art capillary pumps onto the surface of porous member 102 are eliminated entirely in the present invention. Housing component 202 therefore does not experience temperatures significantly exceeding the liquid vaporization temperature, nor does the fabrication material for housing component 202 need to possess good thermal conductivity as contrasted with orifice components of the prior art. This aids in reducing the complexity and cost of manufacture of housing component 202, and allows for the use of less expensive materials such as aluminum and plastic, as well as combinations of the foregoing. Other acceptable materials for housing component 202 may also be used, as will be recognized by those skilled in the relevant art.

Another advantage of the embodiment of the present invention illustrated at 300 is that heat is applied directly to porous member 102. The result is that there is minimal heating of unnecessary thermal mass, with the concomitant effect that response times of the device are improved as compared with prior art capillary pumps. Another advantage of the embodiment shown at 300 is that heater 104 is in more intimate contact with the heat sink, that is, the liquid held within porous member 102 by capillary force. The result is that the maximum heater temperature reached during operation of device 300 at a given power density, that is, for a given output flow rate, is reduced as compared to prior art capillary pumps. This improves heater reliability and lifetime, and increases overall energy efficiency of device 300. See the comparative Examples and the data in Table 1, below.

Where heater 104 comprises an electrical resistance heater, it can be formed in different ways. In one embodiment contemplated by the present invention, heater 104 is comprised of a metal wire or etched metal foil present in a configuration that may be characterized as serpentine, coiled or zig-zag, as well as a combination of any of the foregoing. Suitable materials for use with heater 104 include, but are not necessarily limited to: nickel and chromium alloys known as nichromes; graphites; thick film heaters also referred to as cermets; titanium; stainless steel and other nickel-base alloys; in addition to many other electrical resistance heating element materials such as transition metal alloys known to those skilled in the art, as well as combinations of any of the foregoing.

According to one embodiment of the present invention, heater 104 is in direct, heat-exchanging contact with porous member 102. In an alternate embodiment, heater 104 and porous member 102 are not situated in direct, heat-exchanging contact, but are disposed on alternate sides of an optional heat exchanger as will be discussed in greater detail below. Regardless of the proximity of heater 104 to porous member 102, it is desirable that heat be delivered as uniformly as possible over the surface of porous member 102 or that component of the capillary force vaporizer with which heater 104 makes heat-exchanging contact. At the same time, it is also desirable that heater 104 not impede the buildup of pressure in vapor containment region 106 or the egress of vapor at orifice 116. This may be accomplished by using a heater component that comprises a thermal conductor having a narrow cross sectional area that is shaped, coiled, patterned, bent or otherwise distributed evenly over the surface of porous member 102. According to another embodiment of the present invention, it is desirable, for performance purposes, to have heater component 104 cover a specified fraction of the surface area of porous member 102. The percentage of the surface area of porous member 102 that should be covered by heater component 104 is preferably between 20% and 80%, more preferably between 25% and 75% and most preferably between 30% and 70%. These ranges tend to depend upon heater type, as will be understood by those knowledgeable in the heater arts.

For improved efficiency, it may also be desirable to have heater component 104 partially or even completely embedded within porous member 102, such that heater component 104 is integral with porous member 102. This can be accomplished, for example, by machining grooves in porous member 102 to a pattern of heating coils of heater component 104, or by casting the porous member material directly around a prefabricated heater element during manufacture. Alternatively, in accordance with another embodiment of the present invention, heater 104 may comprise a layer of porous heating element material that provides more uniform heat distribution while allowing ready vapor egress across the entire surface of porous member 102. In a different embodiment of the present invention, heater 104 is comprised of a thick film heater produced by depositing and firing a positive temperature coefficient paste, such as a thermistor, directly onto the surface of porous member 102. The bonding of such thick film heaters directly onto the porous member may be achieved during fabrication by stenciling, screen-printing or other line or pattern-printing technologies as will be recognized by those skilled in the relevant art.

Many applications for the capillary force vaporizers contemplated by the present invention require high output from the smallest possible device. Accordingly, it is also desirable to maximize the power density capability of heater component 104. Unfortunately, higher heater power densities often compromise heater reliability and heater lifetimes, therefore an optimum range of power density exists. Capillary force vaporizers of the present invention preferably comprise electrical resistance heaters having a reliable range of operating power density from 1 watt/in$^2$ to 500 watts/in$^2$ (0.16 watts/cm$^2$ to 77.5 watts/cm$^2$), more preferably from 5 watts/in$^2$ to 400 watts/in$^2$ (0.78 watts/cm$^2$ to 62 watts/cm$^2$), and most preferably from 10 watts/in$^2$ to 350 watts/in$^2$ (1.55 watts/cm$^2$ to 54.3 watts/cm$^2$).

Figure 4:
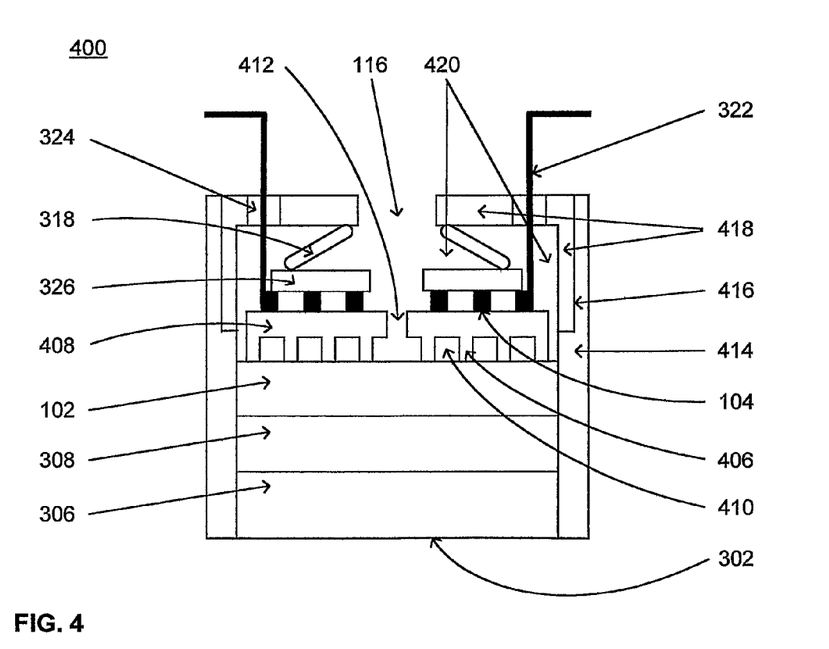
FIG. 4 is a schematic cross sectional view of a capillary force vaporizer in accordance with a fourth embodiment of the present invention.

FIG. 4 shows another embodiment of the present invention at 400. Device 400 is similar to device 300 in that the peripheral seal of prior art devices is completely eliminated. Unlike device 300 however, housing components 414 and 418 in embodiment 400 surround, but do not necessarily require, a compressive mechanical force against, the stacked porous components of 400, namely: optional liquid supply component 306, optional thermal insulation component 308, and porous member 102. At least one of the housing components, for example housing component 418 in the device 400, comprises one or more orifice(s) 116 but housing components 414 and 418 no longer provide a vapor containment function. Optional heat exchanger 408 has been added between heater 104 and porous member 102. Optional spring component 318 is used to provide a sufficient compressive mechanical force between heat exchanger component 408 and porous member 102 such that leakage of vapor or liquid from device 400 is effectively prevented. Optional support insulator 326 may be used to ensure complete and intimate contact between heater 104, optional heat exchanger 408 and porous member 102. Optional heat exchanger 408 further comprises contacts 406, which in turn comprise: fins, posts, vanes, teeth or constructs of similar features, as well as any combination of the foregoing, that contact and conduct heat from heater component 104 to the interface between porous member 102 and heat exchanger 408. Optional heat exchanger 408 also further comprises channels 410 that serve as vapor containment regions by collecting and pressurizing vapor produced by device 400, and one or more orifices 412 to direct the pressurized vapor away from porous member 102 and toward orifice 116 of housing component 418.

Note that in contrast to device 300 in FIG. 3, where vapor containment region 106 was created by voids between adjacent porous member 102 and heater component 104, the vapor containment region in device 400 is present in the form of vapor containment volume 410, situated between optional heat exchanger 408 and porous member 102. The previous description for the percent of surface area of porous member 102 in contact with heater 104 in device 300 now applies, instead, to the surface area between contacts 406 of optional heat exchanger 408 and porous member 102. The same holds true for optional heat exchanger 408 and porous member 102 in devices 500, 600 and 700 of FIGS. 5A, 6 and 7, respectively. Thus, the percentage of the surface area of porous member 102 occupied by contacts 406 of optional heat exchanger 408, for example, in devices 500, 600 and 700, is preferably between 20% and 80%, more preferably between 25% and 75% and most preferably between 30% and 70%. Again, these ranges tend to depend upon heater type, the properties of optional heat exchanger 408, and characteristics of the porous member 102, as will be understood by those knowledgeable in the heater arts.

Another distinction between inventive device 300 and inventive device 400 is the presentation of capillary force vaporizer 400 as having separable components, namely first or upper housing 418 and second or lower housing 414. A separable housing design facilitates assembly of device components during manufacturing, and also allows device 400 to be disassembled and reassembled for field service, repair or component replacement, should the latter become necessary. This provides an advantage over prior art capillary pumps. Previous devices were comprised of layered structures wherein layers became permanently bonded together by a peripheral seal during production and therefore could not be separated once the device was manufactured. Consequently, it was not possible to replace any of the individual internal components should they become fouled or otherwise inoperable, and upon occasion, the entire device had to be replaced. Many well-known means for engaging upper housing 418 and lower housing 414 at mating interface 416 can be contemplated for use with the present invention. Such techniques include, but are not limited to: friction fittings, snap closures, bayonet attachments, threaded screw closures, twist lock closures, as well as combinations of any of the foregoing, as will be appreciated by those knowledgeable in the relevant art.

The use of optional heat exchanger 408 allows very high power density heaters, whose preferable output range as described previously (see paragraph 38 above) is used internal to inventive capillary force vaporizer 400. The use of the preferable high power density heaters described, in combination with optional heat exchanger component 408, provides very uniform heat distribution on the surface of porous member 102 and simultaneously allows hot pressurized vapors generated within device 400 to be advantageously collected and directed away from the walls of upper housing 418 and lower housing 414 during egress. Provided that orifice 116 of upper housing 418 is located and sized appropriately, that is, preferably aligned above and having dimensions greater than those of orifice 412 in optional heat exchanger 408, this embodiment makes it possible to prevent hot pressurized vapor from coming into contact with housing members 418 and 414. Consequently, housing members 414 and 418 do not need to exhibit resistance to high temperatures, advantageously enabling the use of inexpensive and easily manufactured materials for the housing members such as plastics and the like.

Optional heat exchanger 408 may be optimized by adjusting the ratio of the area of contacts 406 to the area of the vapor containment region or channels 410 at the interface between optional heat exchanger 408 and porous member 102, and by minimizing the total thickness of optional heat exchanger 408 in order to minimize the temperature gradient between heater 104 and porous member 102. The percentage of surface of optional heat exchanger 408 occupied by contacts 406 is the same as the preferred surface area coverage described above for heater 104. That is, contacts 406 of optional heater 408 comprise preferably from 20% to 80%, more preferably from 30% to 70% and most preferably from 40% to 60% of the surface area at interface 409 (not illustrated) between optional heat exchanger 408 and porous member 102. The thickness of optional heat exchanger 408, that is, the total distance from heater 104 to porous member 102 is preferably from 0.01 mm to 5 mm, more preferably from 0.01 mm to 3 mm and most preferably from 0.01 to 2.5 mm.

The volume disposed towards the interior of device 400, defined by upper housing 418 and lower housing 414, shown at 420, no longer acts as a vapor containment region in device 400. Instead, volume 420 serves as an insulating air gap between optional heat exchanger component 408 and housings 418 and 414. Therefore, housing members 414 and 418 remain significantly cooler than analogous sheaths, containment means or housing means in prior art devices, even when operating device 400 at very high power levels with high boiling point fluids. (See the comparative Examples and data in Table 1, below.) Lower exterior surface temperatures on devices such as 400 offer significant safety and reliability advantages compared to prior art devices. In addition, this embodiment completely overcomes the prior art limitation of poor device reliability since device 400 no longer relies upon thin, often brittle peripheral seals for primary structural support. Such seals were often prone to failure with prior art devices. And, since upper and lower housing members 414 and 418, respectively, remain cooler than prior art devices, another advantage of the present invention is that housing members 418 and 414 can be made from strong, easily manufactured and inexpensive materials such as aluminum, plastics, and the like.

Figure 5A:
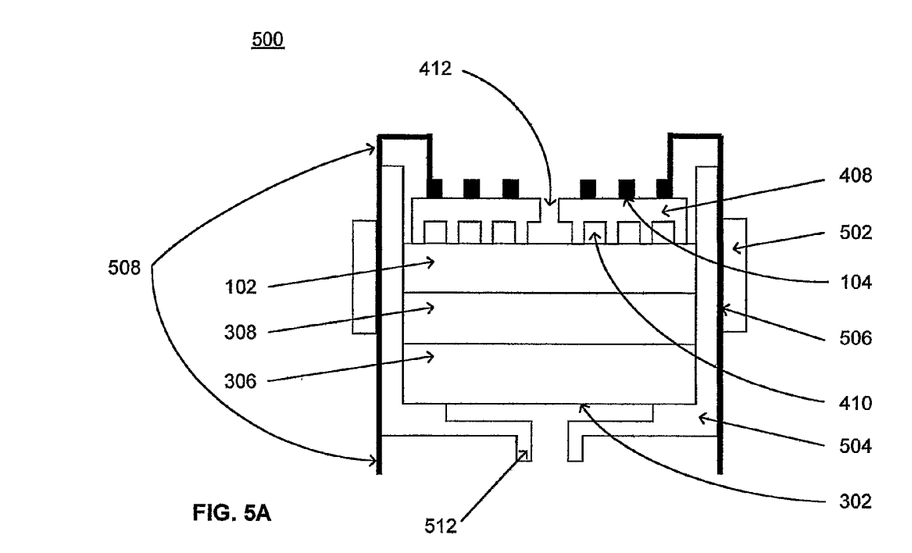
FIG. 5A is a schematic cross sectional view of a capillary force vaporizer in accordance with a fifth embodiment of the present invention.

FIG. 5A shows another embodiment of the present invention at 500. Device 500 is similar to device 400 except that device 500 features a separable housing comprising first or outer housing 502 and second or inner housing 504. As stated above, a separable housing design facilitates assembly of device components during manufacturing, and also allows device 500 to be disassembled and reassembled for field service, repair or component replacement, as necessary or desired. Techniques for engaging outer housing 502 and inner housing 504 at mating interface 506 are well known and have been discussed previously with reference to inventive device 400. Devices 400 and 500 thus present alternate embodiments of separable housings as contemplated by the present invention: upper and lower housings 418 and 414, respectively, of device 400; and outer and inner housings 502 and 504, respectively, of device 500. These as well as any number of variations on separable housings, such as the location or the number of separations, etc., are contemplated by and fall within the scope of the present invention as will be appreciated by those knowledgeable in the relevant art.

Another feature of device 500 as compared to device 400 is that a portion of upper housing 418 in device 400, namely that portion that contained orifice 116, has been entirely eliminated in device 500. By locating the housing away from the top surface of the CFV, there is no longer a need to insulate housing material opposite the orifice and the need for air volume 420 is therefore eliminated. This simplification is possible since vapor containment occurs at channels 410 of optional heat exchanger component 408, and vapor egress is now controlled by and occurs at orifice 412 in device 500. Note further that the liquid feed mechanism notwithstanding, CFVs of the present invention may be run in any orientation.

An additional feature of device 500 was achieved by combining the functions of electrical leads 322 and optional spring component 318 in device 400 into a single element, namely mechanical force generating conductor 508 in device 500. Thus, mechanical force conductor 508 has been configured to wrap downward and extend to a distal region of device 500, where electrical connections can be made, opposite to orifice 412 where pressurized vapor exits device 500. This embodiment is possible providing the material used to produce spring conductor component 508 is both a good electrical conductor and exhibits a high elastic modulus. Suitable materials for construction of mechanical force generating conductor component 508 include: various metals and metal alloys of, for example, titanium and nickel; high carbon steels and stainless steels; plastics; as well as combinations any of the foregoing. Device 500 thus eliminates the need for separate spring component 318 and optional support insulator component 326 of the device shown at 400, which reduces cost and facilitates easy assembly.

Figure 5B:
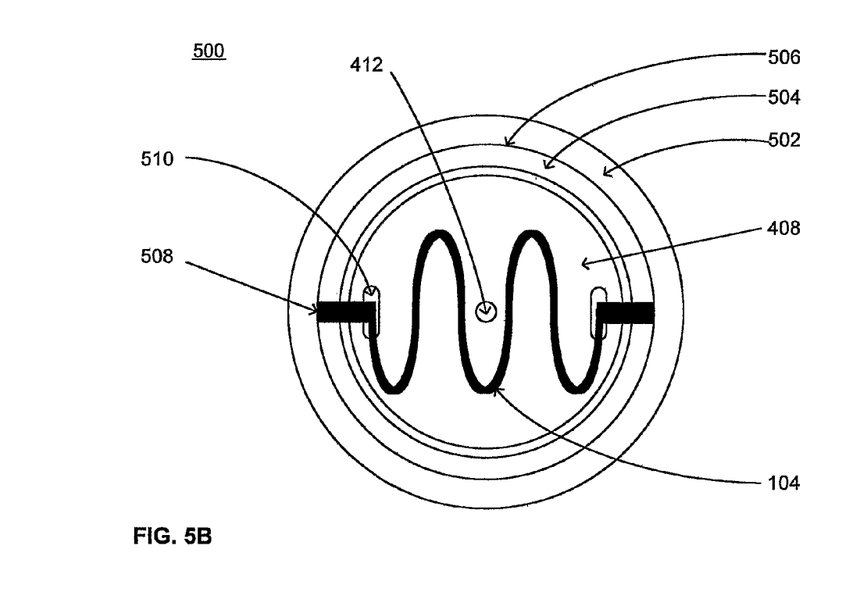
FIG. 5B is a top view of the capillary force vaporizer shown in FIG. 5A.

Further, as shown in FIG. 5B, mechanical force generating conductor component 508 need only contact optional heat exchanger 408 in a diametrically opposed pattern in order to provide sufficient compressive mechanical force. This allows electrical connections to heater component 104 to be made by spring conductor components 508 at discrete locations 510 of heat exchanger 408, facilitating improved heater circuit design and minimizing heat loss. Notice also in device 500 that outer housing 502, by virtue of the fact that it removably attaches circumferentially to inner housing 504, provides a mechanical support function for mechanical force generating conductor component 508 to ensure that compressive mechanical forces between heat exchanger component 408 and porous member 102 are sufficient to prevent loss of liquid and vapor from vapor containment regions at channels 410. Inner housing 504 further comprises optional attachment region 512 for use in attaching device 500 to an optional liquid supply line (not shown). A process for manufacture of a capillary force vaporizer device for the vaporization of liquid and the pressurization of vapor according to one embodiment of the present invention may therefore be regarded as comprising:

1. providing a porous member, the porous member comprising a capillary network, a surface for receiving liquid, and a vaporization area in which vapor is produced from the liquid;
2. providing a heater component for conveying heat to the porous member, the heater component further optionally comprising a heat exchanger; and
3. providing a vapor containment component, the vapor containment component comprising a vapor containment region for the collection and pressurization of the vapor, a mechanical force conductor and at least one orifice for the release of the vapor, wherein the mechanical force conductor provides compressive force among the porous member, heater component and vapor containment component.

Figure 6:
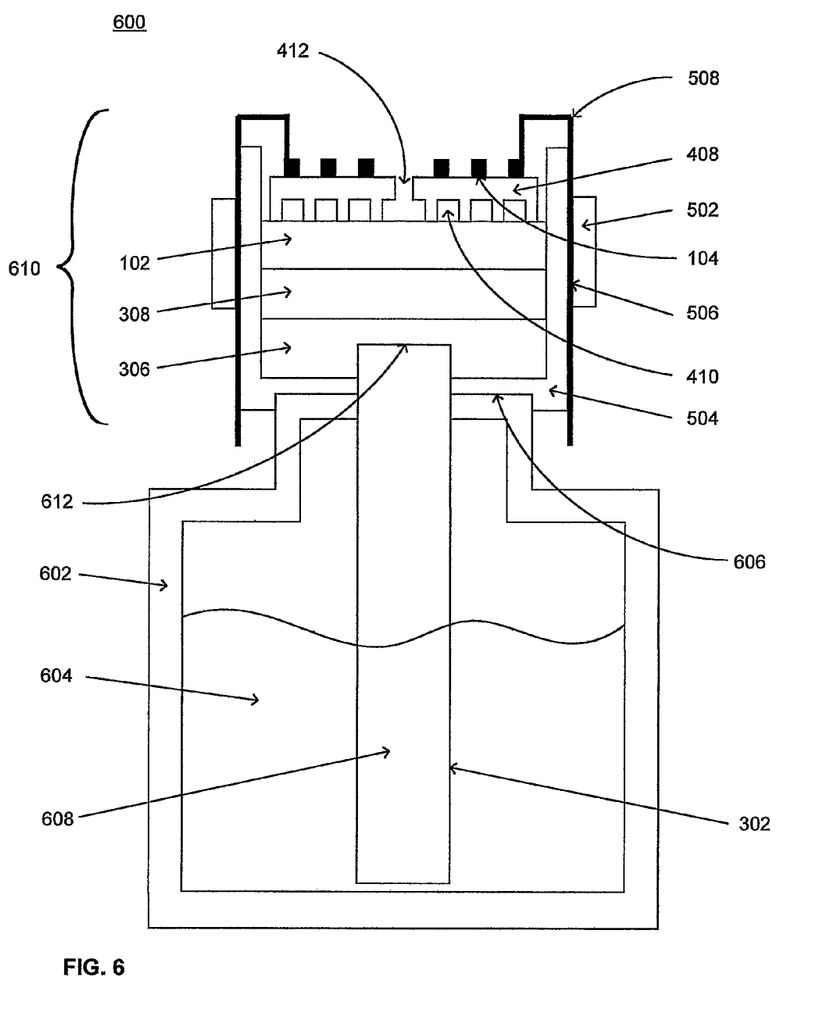
FIG. 6 is a schematic cross sectional view of a capillary force vaporizer in accordance with a sixth embodiment of the present invention.

FIG. 6 shows another embodiment of the present invention, in which a liquid vaporization and pressurization system is fully integrated with optional liquid supply and liquid feed elements. In this example, system 600 includes a capillary force vaporizer module at upper assembly 610 in liquid supply contact with removable liquid reservoir 602. Note that the term "module" is used herein to pertain to components in addition to a single CFV. Thus, a module may refer to a collection of two or more CFVs in use together as well as the additional components and parts that include a single CFV in a particular application. Reservoir 602 contains liquid to be vaporized 604 and connects directly to inner housing 504 at mating interface 606. In an alternate embodiment of the present invention (not shown), where no separable housing is used, reservoir 602 would connect, for example, directly to housing 504 at a distal end of a device as shown in FIG. 5a. As will be readily appreciated by those knowledgeable in the relevant field, a number of techniques may be used to matingly engage reservoir 602 with lower housing 504. These may be similar to the techniques described previously for matingly engaging outer and inner housings 502 and 504, respectively, in FIG. 5.

Optional wick component 608 in FIG. 6 is part of, and remains affixed to, reservoir 602 and is designed such that wick extension 612 of optional wick component 608 ensures good intimate contact with upper assembly 610 via optional liquid supply component 306, optional thermal insulation component 308 or porous member 102. In this embodiment, liquid feed surface 302 extends throughout reservoir 602 to ensure that all liquid can be utilized.

Wick component 608 may serve not only as a capillary wick for supplying liquid to porous member 102, optional liquid supply component 306 or optional thermal insulation component 308 as illustrated in FIG. 6, but may also serve as a cap or closure for liquid reservoir 602 to prevent spilling or leaking of reservoir contents when liquid supply reservoir 602 is disengaged from lower housing 504. In practical commercial designs, liquid vaporization and pressurization system 600 can be provided as two subassemblies joined together. Alternately, liquid reservoir 602 with wick component 608 can be provided as a removable, replaceable or disposable refill cartridge, separate from upper subassembly 610.

Other similar and obvious variations of the configuration for the capillary force vaporizer illustrated in FIG. 6 are also contemplated herein. For example, optional wick component 608 and reservoir 602 may be separable. Alternately, it may be advantageous to incorporate all of the porous material components into one assembly, for instance, optional liquid supply component 306, optional thermal insulation component 308, porous member 102 and liquid reservoir 602 may comprise one sub-assembly, leaving electric heater 104, optional heat exchanger 408 and lower housing 504 as a second subassembly. Alternately, housing 504 with liquid reservoir 602, liquid 604 and optional liquid supply component 306 can be used in lieu of the first subassembly described above. In yet another alternate embodiment, the capillary force vaporizer of the present invention may comprise multiple subassemblies. These would include: (a) a heater subassembly, comprising electric resistance heater 104, optional heat exchanger 408 and outer housing 502; (b) a vaporization subassembly, comprising an intermediate housing (not illustrated), porous member 102 and optional thermal insulation component 308; and (c) a removable liquid supply subassembly, comprising liquid reservoir 602 and optional wick component 608.

Figure 7:
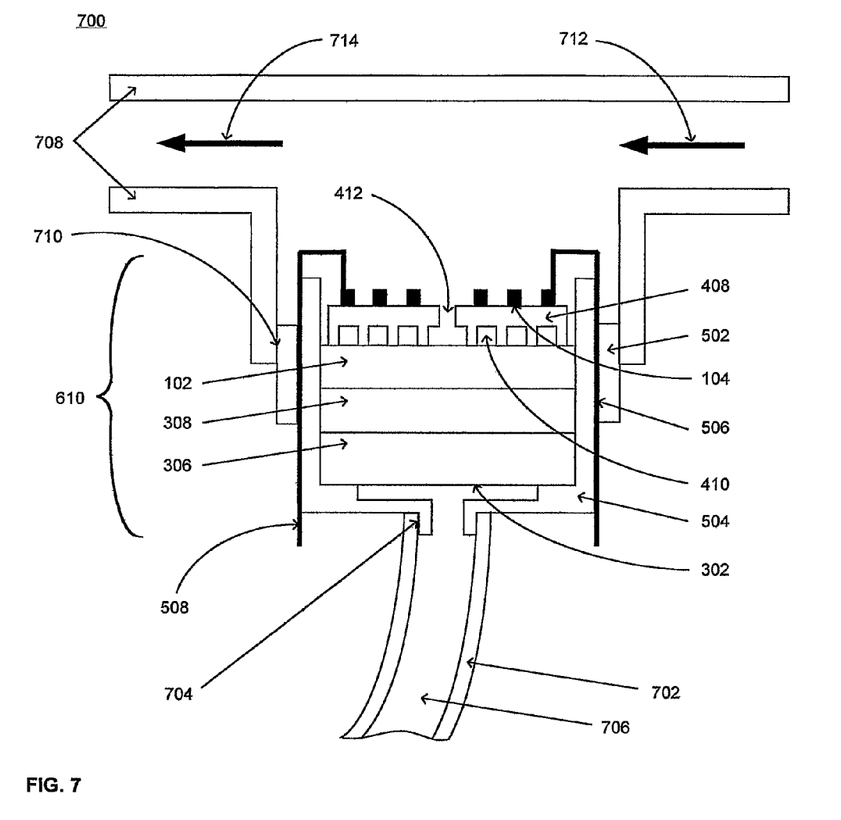
FIG. 7 is a partial schematic cross sectional view of a capillary force vaporizer system in accordance with a seventh embodiment of the present invention.

FIG. 7 shows another embodiment of the present invention. In this embodiment, device 700 includes exemplary capillary force vaporizer module upper assembly 610 having inner housing 504 matingly engaged to a proximal end of liquid supply component 702 at mating interface 704. In one embodiment, liquid supply component 702 comprises a hose that delivers liquid 604 to liquid feed surface 302.

In FIG. 7, liquid supply component 702 supplies liquid 604 (not shown) to liquid feed surface 302 of assembly 610. A supply of liquid can be maintained by any conventional method known to those skilled in the art including, but not limited to: gravity feed; pumps; flow meters; and the like (not illustrated); as well as combinations of any of the foregoing. Note that the supply of liquid to the CFV may be either continuous or intermittent. Other embodiments are contemplated in which an optional wick may be used between liquid feed surface 302 and liquid 604. A distal end of liquid supply component 702 may engage a gravity feed reservoir such as an elevated storage container or a hanging flexible bag (not illustrated). Additionally, system 700 may optionally incorporate various flow meters, valves and the like known to those skilled in the art in order to monitor system performance and allow convenient or automated operation. This type of system is well-suited for applications such as humidification of in-hospital patient ventilator circuits and continuous positive airway pressure (CPAP) devices. In typical CPAP device operation, liquids, such as water, are transported and stored in flexible bags with industry standard medical hose connections.

In the embodiment shown, device 700 also incorporates optional adapter 708 that engages capillary force vaporizer module 610 to direct pressurized vapor into a cross flow of fluid. In one embodiment, the fluid cross flow may comprise air generated by a remote pump or compressor (not shown). In one example of the present invention, typical of a medical humidification device in which module 610 is used to vaporize water, dry air 712 entering adapter 708 is mixed with water vapor that emerges from capillary force vaporizer module 610 at orifice 412 and exits adapter 708 as flow of moist air 714. Output control of capillary force vaporizer 610 relative to the flow of dry air allows improved control over the relative humidity of moist air flow 714.

Figure 8:
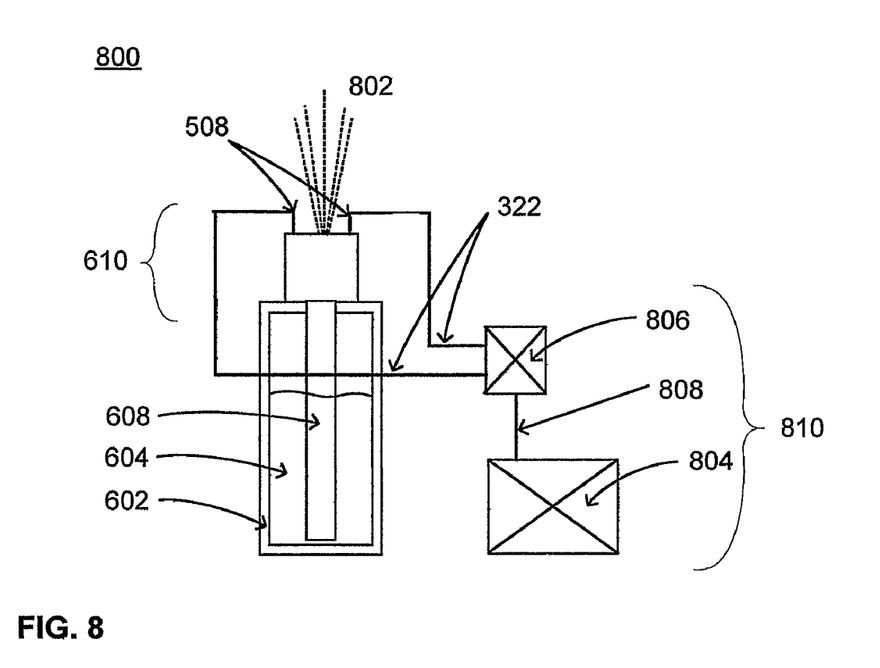
FIG. 8 is a schematic view of a capillary force vaporization system according to an eighth embodiment of the present invention.

In addition to the embodiments and adaptations comprising capillary force vaporizer modules already disclosed herein, the present invention also contemplates device integration of the inventive capillary force vaporizers into fully functional capillary force vaporizer systems. FIG. 8 illustrates one such embodiment in which capillary force vaporizer system 800 comprises capillary force vaporizer upper assembly 610, optional liquid reservoir 602, liquid to be vaporized 604, optional wick component 608 and control circuit 810. Control circuit 810 further comprises power supply 804, controller 806 and communication link 808. Optional liquid supply component 602 in FIG. 8 may comprise a container.

Power supply 804 of device 800 provides electrical energy to drive resistance heater 104 (not illustrated) of capillary force vaporizer upper assembly 610. Power supply 804 is connected to heater 104 via electrical leads 322 that mate to spring conductor components 508, such that when power supply 804 is energized, vaporization of liquid and pressurization of vapor results in the generation of vapor 802 emanating from device 800. The flow rate of vapor 802 is approximately proportional to the input power level. Controller 806 is in electrical communication with power supply 804 via communication link 808 to ensure that power supply 804 delivers the appropriate voltage and current characteristics to heater 104, and allow for variable output control when operating system 800. The specific requirements for power supply 804, for instance AC versus DC power, maximum power, etc., and control circuit features, such as manual versus automatic control of power level, power conditioning, programmed ramps and set points, temperature sensing capability, and the like, depend on the particular application requirements for device 800. Of particular importance in determining the type of power supply and control circuit are liquid properties, desired vaporization rate, accuracy of control needed, and anticipated system cost.

In general, the individual components comprising the power supplies, controllers and circuits of the type contemplated for use with the capillary force vaporizer systems of the present invention will be well known to those skilled in the art. For operation of devices at very high flow rates, with a continuous duty cycle, or when sophisticated variable output control is desired, an AC powered circuit is most preferred. In many straightforward cases, power supplied by a 110V or 220V AC wall outlet may be used. Control circuit 810 can provide the necessary line voltage step-down and/or power conditioning to allow capillary force vaporizer module 610 to operate.

Control circuit 810 may comprise various known electronic methods and include, for example, analog circuits such as those found in potentiometers and digital circuits that feature pulse width modulation, as may be understood by those skilled in the relevant art. In other applications, separate power supply units that plug into wall outlets and also connect to capillary force vaporizers may be used for element 804. In still another embodiment, power supply 804 may comprise one or more self-contained power sources such as batteries. Examples of such power sources include, but are not necessarily limited to: nine volt batteries; D cells; nickel-cadmium (Ni-Cad), and lithium-ion (Li-ion) batteries; as well as other disposable and rechargeable batteries, in addition to combinations of any of the foregoing. Battery power sources may be preferred, for example, in applications requiring low flow rates or only intermittent duty cycles involving short pulses or bursts of vapor 802, or when portability of a device is desired. In such cases, simple capacitive discharge timing circuits well known to those skilled in the art can be employed to provide useful battery life and stable system operation.

As will be apparent to those knowledgeable in the relevant field, in certain implementations of the capillary force vaporizers and capillary force vaporizer systems of the present invention, it may be desirable to incorporate power supply 804, controller 806, and communication link 808, either singly or taken in combination, into a single unit, which may be attached either directly or remotely to the inventive capillary force vaporizer module. Thus, in yet another embodiment of capillary force vaporizer systems contemplated herein, the entire system comprising capillary force vaporizer module, liquid supply and feed, power supply, and control circuit may all be integrated into a single assembly. Various embodiments and examples of systems that incorporate the inventive capillary force vaporizers are further illustrated by way of the following Examples.

Example 1

A capillary force vaporizer module was manufactured according to the embodiments of the present invention as shown in FIG. 4. The diameter of porous member 102 was 19 mm and its thickness was 1 mm. The external diameter of the device was about 30 mm. The porous member and insulator component were fabricated from highly porous alumina using known techniques. See, for example, U.S. Pat. No. 6,585,509 and U.S. Pat. No. 6,634,864. The vaporizer material had a mean pore size of about 1 micron (μm) and the total porosity was about 80%. The insulator component had a mean pore size of about 20 μm and the total porosity was about 80%. The heat exchanger component was manufactured from approximately 96% dense aluminum oxide, and the material, design and manufacturing methods were similar to those used to manufacture the orifice component in prior art CFV devices.

The external housing in Example 1, which comprised upper and lower housing sections, was made from Teflon plastic by standard machining methods. The remaining elements of device 400 stacked layer components were sized appropriately to provide a tight friction fit when inserted into the external housing, thereby assuring intimate contact between the stacked layer components during operation. For purposes of allowing a direct comparison of performance improvements attributable solely to the embodiments of the present invention compared to prior art devices, the porous member, thermal insulation component and liquid supply component in Example 1 were substantially equivalent to those used in the comparative prior art devices.

The electrical resistance heater used in the device of the present invention was a thick film resistor type heater with a maximum power density of about 300 watts/in$^2$ (46.5 watts/cm$^2$). An identical heater was used to provide heat externally to the comparative prior art device of this example.

The capillary force vaporizer module of Example 1 was connected to a 200 watt power supply that was controlled by a software program via computer interface, thus forming an integrated capillary force vaporizer system as shown in FIG. 8. Using distilled water as a test liquid, the device of the present invention was operated successfully, producing a stable jet of water vapor over a wide range of power settings. The device was operated from about 20 watts up to the maximum achievable power level of about 150 watts in increments of 10 watts, and the performance of the device was recorded. The output flow rate of the device increased linearly with applied power over the range tested, and temperature measurements at the bottom of the device indicated no heat was propagating downward into the liquid supply, a requirement for stable capillary force vaporizer operation.

The performance of the inventive device was then compared with that of a capillary pump of the prior art as described in U.S. Pat. No. 6,634,864. As discussed, for purposes of comparison, the prior art device had substantially equivalent porous material components and physical dimensions, but was held together with a vitreous glazing comprising a thin glass layer, to form an impermeable peripheral seal. The prior art device was operated over approximately the same power range by placing an identical electrical resistance heater on the top (external) surface of the orifice component. Comparative results obtained for the two devices are shown in TABLE 1.

TABLE 1

Performance Characteristics Using Distilled Water

| Parameter | Prior Art Device | Present Invention |
|---|---|---|
| Response time, in sec (±0.5 sec) | 7 | 2-3 |
| Thermodynamic efficiency, in % (±2%) | 78 | 93 |
| Maximum exterior surface temperature at top of device, in ° C. (±5° C.) | 250 | 69 |
| Maximum heater temperature at 100 watts, in ° C. (±5° C.) | 368 | 177 |
| Flow rate at 100 watts, in g/min (±0.1 g/min) | 1.8 | 2.2 |
| Comments on Reliability/Cracking | Cracking of peripheral glaze | No reliability issues |

The device of the present invention exhibits improved performance in all categories, and as indicated at the last entry of TABLE 1, the cracking/reliability problem of the prior art devices has been completely eliminated.

Examples 2a and 2b

A capillary force vaporizer module was manufactured according to the embodiment of the present invention shown in FIG. 5A. Both the outer and inner housing components, corresponding to 502 and 504, respectively, of FIG. 5A, in Example 2a were machined from aluminum metal, and a simple set screw was used to hold the components together. The capillary force vaporizer module of this example was connected to a 200 watt power supply that was controlled by a software program via computer interface, thus forming an integrated capillary force vaporizer system as shown in FIG. 8. Using distilled water as a test liquid, the device was operated successfully over a wide range of power settings similar to Example 1 above and the performance characteristics were recorded. Within the margins of measurement errors, the device performance characteristics were found to be essentially identical to those of the present invention device of Example 1, as shown in Table 1, with the exception that the maximum exterior surface temperature was measured at the periphery and near the top of inner housing 504.

The device of Example 2a was then disassembled by loosening the set screw to separate the two housing components and remove all the individual components. The stacked layer components were easily removed and inspected. The electric resistance heater and porous member were replaced with new, essentially identical components, and the device was re-assembled to provide Example 2b. Upon re-assembly and repeating the test under identical conditions with Example 2b, the device performance characteristics were again found, within the measurement errors, to be essentially identical to those shown for the inventive device of Example 1 as well as those of Example 2a prior to disassembly and consistent with the results presented in Table 1. It should be noted, in comparison, that sealed capillary pumps of the prior art cannot similarly be readily disassembled and reassembled.

Example 3

Next, a complete vaporization system as shown in FIG. 7 was assembled as follows. The liquid supply component was removed from the capillary force vaporizer of Example 2b. A custom fitted liquid supply component made from the same material was machined so that one end of the liquid supply component fit directly into the end of a polyethylene liquid supply hose that was connected to a flexible gravity feed reservoir. The other end of the liquid supply component was machined to fit directly into the bottom of the capillary force vaporizer such that when fully assembled, the capillary force vaporizer was connected directly to the liquid supply hose using the liquid supply component to hold the system together.

The system and device of Example 3 was operated successfully over the same range of conditions as in Example 1, and, within the measurement errors, the performance characteristics were essentially similar to those shown previously in Table 1 for Example 1 as well as Example 2a prior to disassembly. Using the capillary force vaporizer of the prior art, it was not possible to assemble and test a comparative system due to the very high exterior surface temperatures and the inability to make a convenient connection with the liquid supply hose.

Example 4

A capillary force vaporizer module was manufactured according to the embodiments of the present invention as shown in FIG. 5. In this example, the diameter of the porous member was increased to 30 mm, compared with the diameter of 19 mm used in the inventive device described in Example 1. The dimensions of the other components were scaled appropriately to accommodate the 30 mm porous member and the device was assembled and tested in the same manner as in Example 1.

The capillary force vaporizer module of the instant example was connected to a 200 watt power supply that was controlled by a software program via computer interface, thus forming an integrated capillary force vaporizer system as shown in FIG. 8. Using de-ionized water as a test liquid, the device was operated successfully over a wide range of power settings and its performance was characterized.

The flow rate achieved for this device was 0.6±0.1 g/min at a power level of about 30 watts. Devices of the prior art, when tested in the same manner, achieved a flow rate of 0.5±0.1 g/min at a power level of 30 watts. Because devices of the present invention have no brittle peripheral seal, conceivably any diameter device can be manufactured and made to operate reliably without failure. With sufficient power density applied over the surface of the porous member of the instant capillary force vaporizers, vapor flow rates proportional to the total power input are expected.

In Example 4, the 30 mm diameter device of the present invention generated a flow rate of 4.4±0.2 g/min at 200 watts, which was the limit of the available power supply. Since this flow rate was not the maximum that the device of Example 4 was capable of handling, it is conceivable that larger power supplies may achieve even higher flow rates. Thus, there appear to be no practical limitation to device size based on reliability concerns for capillary force vaporizers of the present invention. Note that it is not possible to manufacture or operate devices of the prior art that are larger than about 19 mm without cracking and premature failure of the brittle peripheral seal. Consequently, flow rates for devices of the prior art having diameters larger than about 19 mm cannot be measured and comparable flow rates to the instant example cannot be achieved. Example 4 thus demonstrates the ability to produce practical capillary force vaporizers having substantially larger sizes, that is, larger porous member surface areas, and concomitantly higher output flow rate capabilities as compared to prior art devices. In one sense, therefore, the size contemplated for a CFV may be limited by the power capabilities of available power sources.

The present invention has been described above in detail with reference to specific embodiments, Figures, Tables and Examples. These specific embodiments should not be construed as narrowing the scope of the invention, but rather as illustrative examples. It is to be further understood that various modifications and substitutions may be made to the described capillary force vaporizer modules and systems, as well as to materials, methods of manufacture and use, without departing from the broad scope of the invention contemplated herein. The invention is further illustrated and described in the claims which follow.

What is claimed:

1. A device for the vaporization of liquid and the pressurization of vapor, comprising:
   a. a porous member comprising a capillary network, a surface for receiving liquid, and a vaporization area in which vapor is produced from the liquid;
   b. a heater component to convey heat to the porous member; and
   c. a vapor containment component comprising a vapor containment region for the collection and pressurization of the vapor, a mechanical force generator and at least one orifice for the release of the vapor;
   wherein the mechanical force generator is external to the porous member, heater component and vapor containment component and provides compressive force among the porous member, heater component and vapor containment component.

2. The device of claim 1, wherein the compressive force is characterized by the deflection of an elastic member.

3. The device of claim 1, wherein the mechanical force generator may be selected from among: mechanical springs, spring systems and clamps including conical washers, wavy washers, bent leaf springs and coil springs; friction fittings; snap closures; bayonet attachments; threaded screw closures; twist-lock closures; welding; chemical, physical or mechanical bonding; sintering; and chemical reaction; as well as combinations of any of the foregoing.

4. The device of claim 1, wherein the porosity of the porous member is between 25% and 95%, preferably between 30% and 90%, and most preferably between 35% and 85%.

5. The device of claim 1, in which the mechanical force generator exhibits an elastic modulus greater than $2 \times 10^9$ kg/m-sec$^2$ ($2.9 \times 10^5$ lbs/in$^2$).

6. A device for the vaporization of liquid and the pressurization of vapor, comprising:
   a. a porous member, the porous member comprising a capillary network, a surface for receiving liquid, and a vaporization area in which vapor is produced from the liquid;
   b. a heater component for conveying heat to the porous member, the heater component further optionally comprising a heat exchanger; and c. a vapor containment component, the vapor containment component comprising a vapor containment region for the collection and pressurization of the vapor, a mechanical force conductor and at least one orifice for the release of the vapor;

wherein the mechanical force conductor is situated external to the porous member, heater component and vapor containment component and provides electrical connection in addition to compressive force among the porous member, heater component and vapor containment component.

7. The device of claim 6, wherein the compressive force is characterized by deflection of an elastic member.

8. The device of claim 6, wherein the mechanical force conductor may be selected from among: mechanical springs, spring systems and clamps, including conical washers, wavy washers, bent leaf springs and coil springs; friction fittings snap closures; bayonet attachments; threaded screw closures; twist-lock closures; laser welding; chemical, physical or mechanical bonding; sintering; and chemical reaction; as well as combinations of any of the foregoing.

9. The device of claim 6, wherein the porosity of the porous member is between 25% and 95%, preferably between 30% and 90%, and most preferably between 35% and 85%.

10. The device of claim 6, in which the mechanical force conductor is characterized as an electrical conductor that exhibits an elastic modulus of at least $2\times10^9$ kg/m-sec$^2$ ($2.9\times10^5$ lbs/in$^2$).

11. The device of claim 6, in which the mechanical force conductor further comprises electrical connections placed at opposite ends of a diameter of a stacked assembly comprising the porous member, heater component and vapor containment component.

12. The device of claim 6, in which the mechanical force conductor is comprised of materials selected from among: metals and metal alloys of titanium and nickel; high carbon steels and stainless steels; plastics; as well as combinations any of the foregoing.

13. A process for assembling a device for the vaporization of liquid and the pressurization of vapor, comprising:
  a. providing a porous member, the porous member comprising a capillary network, a surface for receiving liquid, and a vaporization area in which vapor is produced from the liquid;
  b. providing a heater component for conveying heat to the porous member, the heater component further optionally comprising a heat exchanger; and
  c. providing a vapor containment component, the vapor containment component comprising a vapor containment region for the collection and pressurization of the vapor, a mechanical force conductor and at least one orifice for the release of the vapor, wherein the mechanical force conductor provides compressive force among and is situated external to the porous member, heater component and vapor containment component.

14. In a capillary device for the vaporization of liquid and the pressurization of vapor comprising a porous member, a heater component and a vapor containment component, the improvement comprising the use of a mechanical force conductor to provide electrical connection in addition to compressive forces among, and external to, the porous member, heater component and vapor containment component.

15. The improvement of claim 14, wherein the compressive force is characterized by deflection of an elastic member.

* * * * *